US00PP29142P2

(12) United States Plant Patent
Hansen et al.

(10) Patent No.: US PP29,142 P2
(45) Date of Patent: Mar. 20, 2018

(54) ***PANICUM* PLANT NAMED 'APACHE ROSE'**

(50) Latin Name: *Panicum virgatum*
Varietal Denomination: Apache Rose

(71) Applicants: Hans A. Hansen, Zeeland, MI (US); Kevin A. Hurd, Austin, TX (US)

(72) Inventors: Hans A. Hansen, Zeeland, MI (US); Kevin A. Hurd, Austin, TX (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 14/757,170

(22) Filed: Nov. 30, 2015

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para

(57) ABSTRACT

The new and distinct cultivar of ornamental grass named *Panicum virgatum* 'Apache Rose' with gray-green foliage that develops rosy-red flushed tips in the fall, upright and compact habit with dense culms and airy panicles of rosy-red, suitable as a potted plant, for multi-seasonal interest mass or specimen landscaping, and for cut flower arrangements.

1 Drawing Sheet

Botanical classification: *Panicum virgatum.*
Variety denomination: 'Apache Rose'.

BACKGROUND OF THE PLANT

*Panicum virgatum* 'Apache Rose', hereinafter also referred by the cultivar name 'Apache Rose' and the "new plant" is a new and distinct cultivar of switch grass. The seed was collected by the inventors in the autumn of 2010 as an open pollinated selection from *Panicum virgatum* 'Cheyenne Sky' U.S. Plant Pat. No. 23,209 at a wholesale perennial nursery in Zeeland, Mich. The single seedling was initially selected from among many for further observation in the summer of 2012 at which time it was assigned the original breeder code HK10-07-01.

BRIEF SUMMARY OF THE PLANT

The plant has been successfully propagated by division at the same wholesale perennial plant nursery in Zeeland, Mich. and found to produce identical plants that maintain the unique characteristics of the original plant in multiple generations. The plant is stable and reproduces true to type in successive generations of asexual reproduction.

*Panicum virgatum* 'Apache Rose' differs from its female parent in that the new plant is taller and has gray-green foliage tipped rosy-red in the fall along with rose-colored panicles compared to the concord-purple colored foliage and cream-colored panicles of 'Cheyenne Sky'.

The nearest comparison variety known to the inventors is 'Prairie Fire' U.S. Plant Pat. No. 19,367. In comparison to the new plant, 'Prairie Fire' is slightly shorter, more open in habit, and colors to a deep wine on a much larger portion of the leaf. Other similar switch grass comparison cultivars are exemplified in Table 1 below including: 'Cape Breeze' U.S. Plant Pat. No. 24,895, 'Cheyenne Sky' U.S. Plant Pat. No. 23,209, 'Haense Herms' (not patented), 'Prairie Fire' U.S. Plant Pat. No. 19,367, 'Rostralbush' (not patented), 'RR1' U.S. Plant Pat. No. 17,944 (more commonly know as

*Panicum* 'Ruby Ribbons'), 'Shenandoah' (not patented), and 'Thundercloud' U.S. Plant Pat. No. 20,665.

TABLE 1

Comparison Table

| CULTIVAR | TOTAL HEIGHT (cm) | INITIAL COLOR | SEA-SONAL COLOR | SEASON OF CHANGE | HABIT |
|---|---|---|---|---|---|
| 'Apache Rose' | 95 | gray green | purple tipped | late July | dense upright |
| 'Cape Breeze' | 75 | dark green | purple tipped | late September | compact upright |
| 'Cheyenne Sky' | 112 | blue green | concord purple | early July | very upright |
| 'Haense Herms' | 100 | green | red purple | early August | upright |
| 'Prairie Fire' | 100 | blue green | deep wine | early July | upright |
| 'Rostrahlbush' | 110 | green | red purple | early August | upright |
| 'RR1' | 55 | blue green | purple red | mid July | compact |
| 'Shenandoah' | 140 | blue green | red purple | late July | arching |
| 'Thundercloud' | 275 | blue green | blue green | none | arching upright |

The following traits of *Panicum virgatum* 'Apache Rose', in combination, have been repeatedly observed in multiple generations of asexually propagated plants and distinguish the new plant from all other switch grass plants known to the inventor:

1. Gray-green foliage that develops rosy-red flushed tips in the fall.
2. Upright and compact habit with dense culms.
3. Airy panicles of rosy-red.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
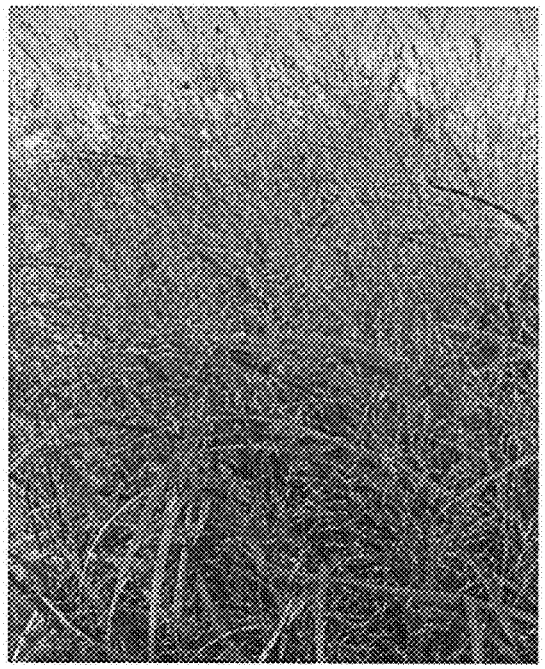
FIG. 1 shows a close-up of the inflorescence in early to mid-August.
Figure 2:
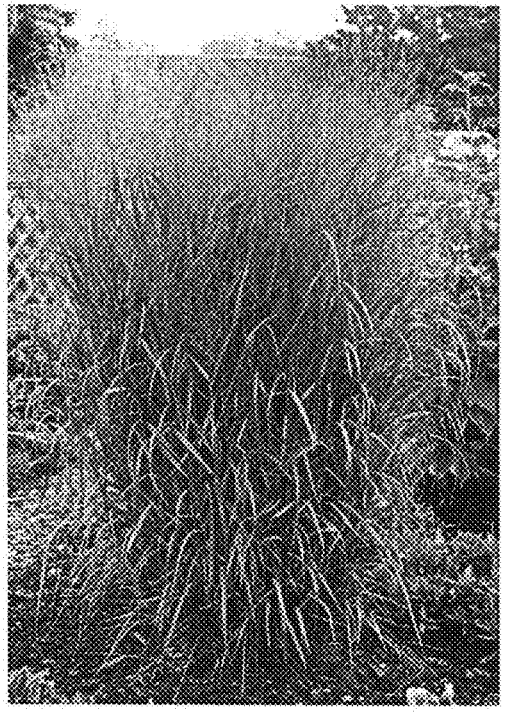
FIG. 2 shows the overall plant in mid-season.

The following descriptions and color references are based on The 2001 edition of The Royal Horticultural Society Colour Chart except where common dictionary terms are used. The new plant, 'Apache Rose', has not been observed under all possible environments. The phenotype may vary slightly with different environmental conditions, such as temperature, light, fertility, moisture and maturity levels, but without any change in the genotype. The following observations and size descriptions are of a four-year old plant in a trial garden of a wholesale perennial nursery in Zeeland, Mich., USA in full sun with supplemental water and fertilizer as needed.

Parentage: Female (seed parent) *Panicum virgatum* 'Cheyenne Sky' (female)×open pollinated (male).

Propagation:

*Method*.—By division of the culms and sterile shoot-tip tissue culture.

*Time to finishing in a* 3.8 *liter pot*.—About three months.

*Rooting habit*.—Normal, coarsely branching; root color nearest RHS 155D.

Plant description:

*Plant shape and habit*.—Hardy herbaceous perennial forming tightly rhizomatous clump, with very upright culms topped with finely textured airy inflorescence producing a narrow clump more than 50 percent taller than wide.

*Plant size*.—Foliage height at flowering is about 63.0 cm tall from soil line to the top of the foliage and 95.0 cm tall to top of flowers; about 18 cm wide at soil line and about 60.0 cm at widest point about 35.0 cm above soil.

Foliage description: Glabrous, with microscopic marginal dentations, flat, alternate along culm, erect through tips, sheathed from node of attachment to ligule, linear; adaxial and abaxial surfaces dull; deciduous but persist through winter.

*Foliage size*.—To about 40.5 cm long and about 13.0 mm wide, shorter at distal end, averaging about 35.0 cm and 10.0 mm wide.

*Foliage color*.—Adaxial surface early season and young foliage: RHS 137A. Abaxial surface early season-and young foliage: closest to RHS 138A. Adaxial surface midseason and later: nearest RHS 137B with some leaves lightly tinted to terminal 50 percent of leaf completely with between RHS N186B and RHS N186C. Abaxial surface midseason and later: portions near the culm of between to RHS N138A and RHS N138B with some leaves lightly tinted to terminal 50 percent of leaf completely with between RHS N186B and RHS N186C.

*Veins*.—Parallel; midrib about 0.5 mm across; abaxial ridged, adaxial recessed; adaxial midrib color between RHS 148B and RHS 148C, abaxial midrib nearest RHS 138A, color of secondary veins same as the surrounding leaf on both the top and bottom of the leaf.

*Culm* (*stem*).—Erect, terete, glabrous, dull surface, 75% enclosed by leaf sheath, about seven nodes per culm; about 120 per clump.

*Culm dimension*.—To about 59 cm long without panicle, average about 52.0 cm; including panicle to about 95.0 cm long with average about 81.0 cm; about 3.5 mm diameter at base; internode length average about 11.2 cm.

*Culm color*.—Lighter than RHS N138D with portions a mixture of between RHS 186C and RHS N187C.

Node description: About 7 per culm, slightly swollen to about 5.0 mm diameter; closest to RHS 199B where receiving full sun exposure, between RHS N189D and RHS N189C where less exposed.

Flower description: Finely branched open panicle, one panicle per culm.

*Flower timing*.—Beginning early August, flowering through late August and panicles dry and remain effective through winter. No fragrance detected.

*Panicle*.—Pyramidal, about 32.0 cm long and 12.0 cm wide; overall effective color RHS 185B.

*Rachis*.—Terete, branched, glabrous, glaucous; about 32.0 cm long and about 1.0 mm at base; branches to about 20.0 cm long and about 0.7 mm diameter held at about 60 degree angle above horizontal; color nearest RHS N138C.

*Pedicel*.—Thin, terete, between 2.0 cm and 5.0 cm long and less than 1 mm diameter; color nearest RHS N138C.

*Rachilla*.—Thin, about 5 mm long and 0.2 mm diameter; color starting RHS 137D and developing to RHS N187A.

*Lower glume*.—About 2.5 mm long and 1 mm wide; color between RHS 187B and RHS 187C.

*Lemma*.—Outer and inner — both about 3.0 mm long and 1.5 mm wide; color between RHS 187B and RHS 187C on surfaces exposed to sun and between RHS 138C and RHS 145B in areas minimally exposed to sun.

*Spikelet*.—Usually with 2 flowers, 1.5 to 2.5 cm long and 2.5 mm wide; flowering on rachis.

*Gynoecium*.—Stigma — two, feathered, protruding about 1.5 mm from glume; color nearest RHS 187A.

*Androecium*.—Filaments — fine, hair-like, white, less than 0.1 mm diameter and up to 2.0 mm long.

*Anthers*.—Two; dorsifixed, longitudinal; about 2.5 mm long and about 1.0 mm wide; color nearest RHS N25A.

*Pollen*.—Round, less than 0.1mm in diameter; nearly transparent, color lighter than RHS 155D.

Fruit: Caryopsis; about 2.5 mm long and about 1.5 mm wide; color nearest RHS 164C.

Hardiness, pest and disease resistance: The plant is very drought once established and rust diseases such as *Puccinia* ssp. have not been observed. Hardiness at least from USDA zone 4 through 9. Disease and pest resistance beyond what is typical of that of other Switch Grasses has not been observed.

We claim:

1. A new and distinct cultivar of ornamental grass plant named *Panicum virgatum* 'Apache Rose' as herein described and illustrated.

* * * * *